United States Patent
Höijer

(10) Patent No.: US 7,908,002 B2
(45) Date of Patent: Mar. 15, 2011

(54) HEART STIMULATOR DETECTING ATRIAL ARRHYTHMIA BY DETERMINING WALL DISTENSION BY IMPEDANCE MEASURING

(75) Inventor: Carl-Johan Höijer, Lund (SE)

(73) Assignee: St. Jude Medical AB, Jarfalla (SE)

( * ) Notice: Subject to any disclaimer, the term of this patent is extended or adjusted under 35 U.S.C. 154(b) by 1290 days.

(21) Appl. No.: 10/540,604

(22) PCT Filed: Aug. 19, 2003

(86) PCT No.: PCT/SE03/01289
§ 371 (c)(1),
(2), (4) Date: May 15, 2006

(87) PCT Pub. No.: WO2004/028629
PCT Pub. Date: Apr. 8, 2004

(65) Prior Publication Data
US 2006/0206157 A1    Sep. 14, 2006

(30) Foreign Application Priority Data
Sep. 30, 2002    (SE) ........................................ 0202882

(51) Int. Cl.
*A61N 1/365*    (2006.01)
(52) U.S. Cl. .............................................. 607/9; 607/17
(58) Field of Classification Search .................. 607/5, 9, 607/17
See application file for complete search history.

(56) References Cited

U.S. PATENT DOCUMENTS

| | | | |
|---|---|---|---|
| 4,865,036 A * | 9/1989 | Chirife | 607/14 |
| 5,720,295 A | 2/1998 | Greenhut et al. | |
| 6,052,624 A * | 4/2000 | Mann | 607/46 |
| 6,070,100 A * | 5/2000 | Bakels et al. | 607/9 |

FOREIGN PATENT DOCUMENTS

| | | |
|---|---|---|
| EP | 0 473 070 | 3/1992 |
| EP | 0 904 802 | 3/1999 |
| WO | WO 98/26839 | 6/1998 |

* cited by examiner

*Primary Examiner* — Niketa I Patel
*Assistant Examiner* — Alyssa M Alter
(74) *Attorney, Agent, or Firm* — Schiff Hardin LLP

(57) ABSTRACT

In an implantable pacemaker, pacing pulses are delivered to a ventricle in a P-wave synchronous mode as long as no atrial arrhythmia is detected, pacing pulses and a mode switch is made to deliver pacing pulses to the ventricle in a non-P-wave synchronous mode if atrial arrhythmia is detected. From an impedance signal measured in the atrium, atrial distention is determined and, in the non-P-wave synchronous mode, the delivery rate of the pacing pulses is increased to decrease the atrial distention during atrial arrhythmia.

5 Claims, 2 Drawing Sheets

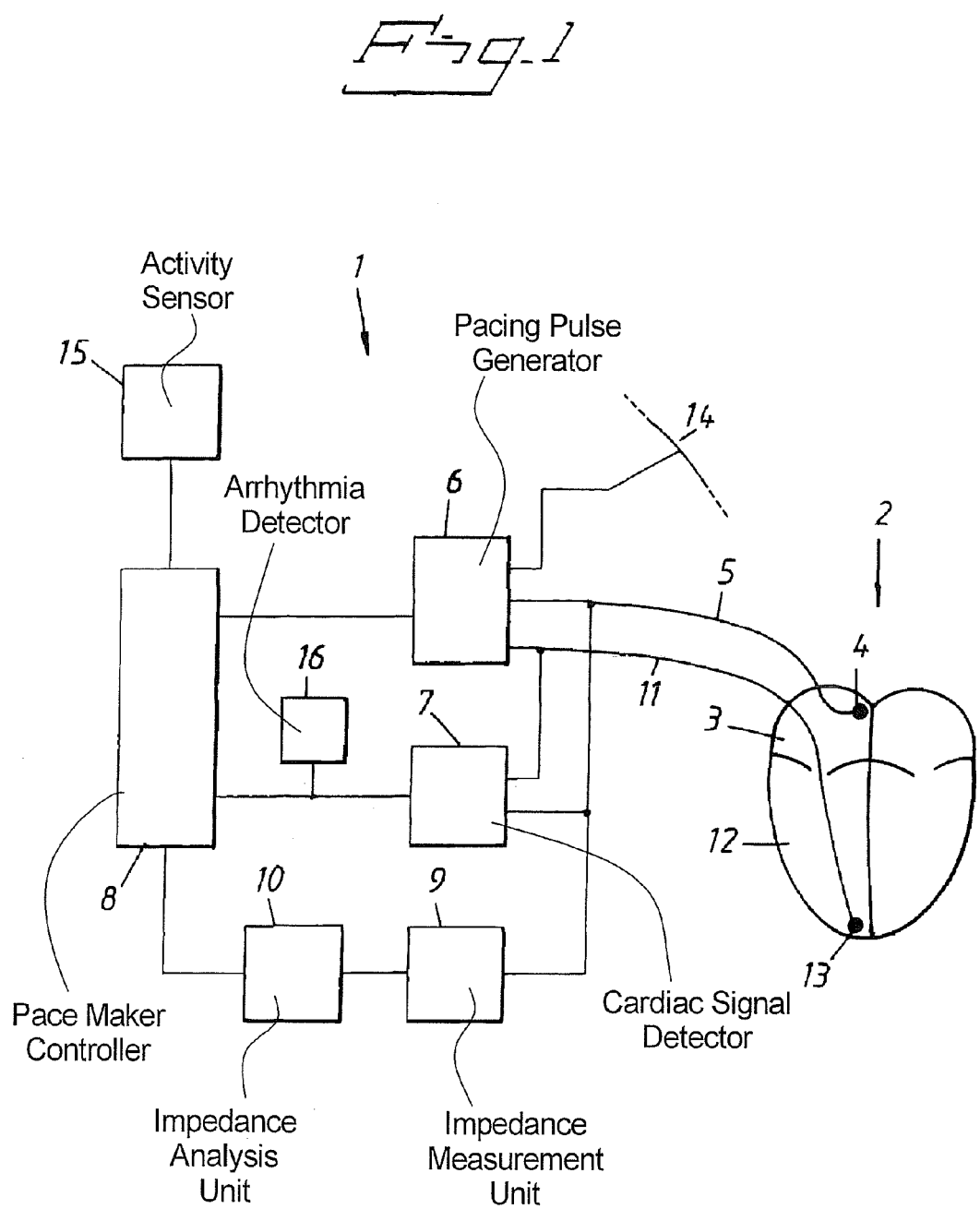

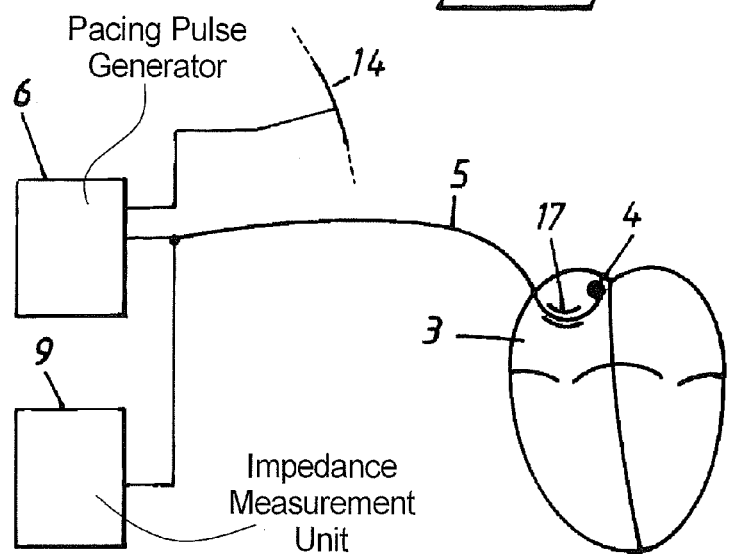
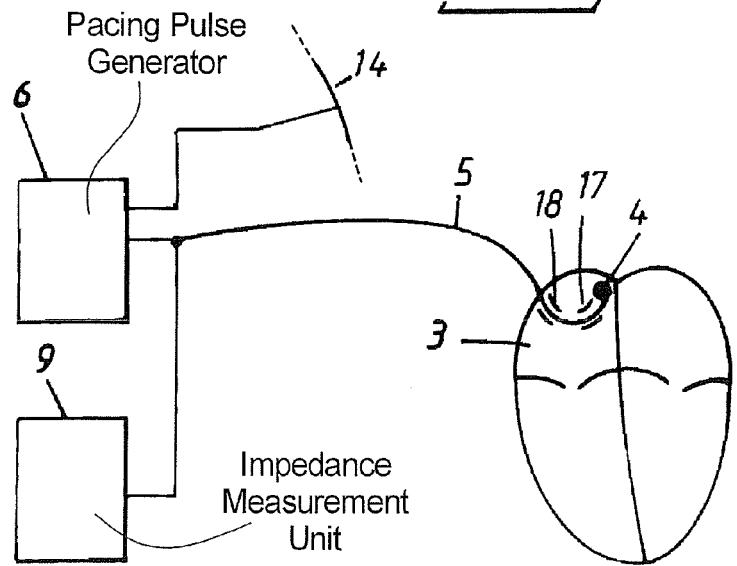

HEART STIMULATOR DETECTING ATRIAL ARRHYTHMIA BY DETERMINING WALL DISTENSION BY IMPEDANCE MEASURING

BACKGROUND OF THE INVENTION

1. Field of the Invention

The present invention concerns an implantable cardiac stimulator of the type wherein pacing of at least one ventricle normally takes place in P-wave synchronous mode, and automatic switching to a non-P-wave synchronous mode takes place if an atrial arrhythmia is detected.

2. Description of the Prior Art

Atrial fibrillation is a very common arrhythmia. During episodes of atrial fibrillation, the systolic function of the atria is lost. This results in distension of the atria which in turn makes it more difficult for the heart to return to sinus rhythm. Without regular systolic activity the atria will only be passive mediators of volume to the ventricles. The degree of distension of the atria will reflect the venous return, i.e. preload.

WO 98/26839 discloses a pacemaker provided with a mode switching feature that stabilizes ventricular heart rate during atrial fibrillation. In response to detection of atrial rhythm characteristics consistent with atrial fibrillation, the device switches into a non-atrial synchronized, ventricular rate stabilization pacing mode. The base ventricular pacing rate is modulated on a beat-by-beat basis based upon preceding intrinsic or paced ventricular heart beat intervals to adjust the pacing interval towards a desired preset rate stabilization target pacing interval which is typically less than the programmed base pacing interval of the device.

U.S. Pat. No. 5,720,295 discloses a pacemaker embodying a mode switch for switching between a first mode wherein synchrony between the atrium and the ventricle is maintained and a second mode wherein pacing is performed at a fixed rate or one determined by the metabolic indicator. This device further monitors the peak amplitude of the atrial intrinsic signals. This information is used to generate short term and long term indicia indicative of the intrinsic signals' variability and deviation from normal sinus rhythm peak amplitudes. The two indicia are combined to generate a single indicia which is then used to categorize the state of the atrium as one of several conditions such as flutter/flubber, coarse atrial fibrillation or fine atrial fibrillation. The categorization is used by a microcontroller for generating the proper pacing pulses and may be also used as a criteria for mode switching.

In a dual chamber pacemaker it is common to include a mode switching feature that causes the pacemaker to switch to a non P-wave synchronous mode if an atrial arrhythmia occurs. The pacing rate may be controlled by a an activity sensor or another more physiological sensor in the event of an atrial arrhythmia.

A problem with prior art mode switching pacemakers is that the atrial contribution is lost during atrial fibrillation and this will cause an increase of pressure of the venous return and thus increased atrial distension during atrial fibrillation. This will in turn make the return to normal sinus rhythm more difficult. It may also increase the risk for future attacks of atrial fibrillation or other atrial tachyarrhythmia.

SUMMARY OF THE INVENTION

An object of the present invention is to provide an implantable heart stimulator that limits the atrial distension, normally caused by atrial fibrillation because of increased atrial pressure, to a level which essentially eliminates atrial remodeling.

The above object is achieved by a pacemaker according to the invention the atrial volume is monitored through an impedance measurement in the right atrium when an atrial arrhythmia occurs. At the implantation or at a later point in time a reference value of the minimum atrial impedance during conditions when no atrial arrhythmia is present is measured. This minimum impedance corresponds to the maximum atrial volume which also corresponds to atrial distension. The determined minimum impedance, and its corresponding atrial distension, is used by the pacemaker as a reference value (ZDIST) for the atrial distension. If the atrial volume increases during AF then the atrial distension also increases. This is observed through the above mentioned impedance measurement. An increased atrial distension is detected as an atrial impedance having a lower value than the reference value ZDIST. If the atrial distension increases, the ventricular pacing rate is increased to allow the atrial distension to decrease to an acceptable level. When the atrial distension measured as an atrial impedance has reached a level close to the reference value ZDIST then the ventricular pacing rate is decreased. In this fashion a closed loop rate responsive control of the ventricular pacing rate during atrial arrhythmia is obtained. During conditions when no atrial arrhythmia is present the rate responsive control is obtained through synchronization to sensed P-waves or through an ordinary rate responsive sensor such as an activity sensor of the accelerometer type or any type of physiological sensor such as a minute volume sensor. This has the advantage that the pacing rate will be adapted to the patient's needs regardless of if the patient has an atrial arrhythmia or not. Since, as mentioned above, the atrial contribution is lost during atrial fibrillation/atrial arrhythmia the ventricular pacing rate may be increased above a rate responsive sensor indicated rate during fibrillation or atrial arrhythmia in order to avoid atrial distension that makes return to sinus rhythm more difficult.

DESCRIPTION OF THE DRAWINGS

FIG. 1 is a simplified block diagram of a dual chamber pacemaker according to the invention.

FIG. 2 shows a lead arrangement with a bipolar atrial electrode for use with the inventive pacemaker.

FIG. 3 shows a lead arrangement with a tripolar atrial electrode for use with the inventive pacemaker.

DESCRIPTION OF THE PREFERRED EMBODIMENTS

FIG. 1 shows a simplified block diagram of a dual chamber pacemaker according to the invention. The patient's heart 2 is connected via atrial electrode 4 and atrial lead body 5 to the pacemaker 1. The patient's heart 2 is also connected via ventricular electrode 13 and ventricular lead body 11 to the pacemaker 1. The pacemaker 1 contains the following functional blocks: pacing pulse generator 6, cardiac signal detector 7, pacemaker controller 8, impedance measurement unit 9, impedance analysis unit 10, activity sensor 15 and pacemaker encapsulation 14. In normal operation the pacemaker controller 8 orders the pacing pulse generator 6 to deliver an atrial pacing pulse via atrial leads 4,5 if no intrinsic P-wave has occurred before the end of the atrial escape interval. The paced or sensed atrial event starts a paced or sensed AV-delay in the pacemaker controller 8. The sensed AV-delay is typically slightly shorter than the paced AV-delay in order to obtain the same delay between the atrial mechanical contraction and the ventricular mechanical contraction irrespective of if it is triggered by a paced or sensed atrial event. If no intrinsic ventricular sensed event occurs before the end of the AV-delay then a ventricular pacing pulse is delivered by pacing pulse generator 6 to the ventricle 12 via ventricular lead formed by the ventricular lead body 11 and ventricular electrode 13. The rate at which the pacemaker controller 8 is operating the pacemaker is modulated by the sensor 15 if the rate responsive function is enabled. If the heart's intrinsic rate is lower than the sensor-modulated rate then the patient will be paced. If the heart's intrinsic rate is higher than the sensor-modulated rate then the pacemaker will be inhibited and no pacing occurs. If an atrial arrhythmia/atrial fibrillation occurs then the arrhythmia will be detected by an arrhythmia detector 16. In response to the atrial arrhythmia the controller initiates a pacing mode change to a non P-wave synchronous pacing mode and further activates the impedance measurement unit 9 and impedance analysis unit 10. The impedance measurement current is injected to the heart via the atrial leads 5,4 with the pacemaker encapsulation 14 used as the return electrode. If the voltage measured between the atrial electrode 4 and the pacemaker encapsulation 14 has been lowered, this indicates that the atrial impedance has been lowered. If the atrial impedance has been lowered this indicates that the atrial volume has increased and that the atrial distension has increased. In response to the increased atrial distension the controller will increase the pacing rate until the atrial distension reaches a lower value similar to that preceding the atrial arrhythmia. During the atrial arrhythmia/fibrillation the pacing rate is controlled in a closed loop system with the atrial distension measured as atrial impedance as feedback parameter. This makes it possible to limit the atrial distension which will minimize negative effects such as atrial tissue remodeling and it will further increase the probability of spontaneous reversion to normal sinus rhythm.

FIG. 2 discloses an alternative current path which uses a bipolar atrial lead formed by the electrode 4, the atrial lead body 5 and a ring electrode 17. The impedance measurement unit 9 injects an impedance measurement current via the atrial lead to the atrium 3. The pacemaker encapsulation 14 is used as the return electrode. The voltage used as the impedance measurement is measured between the atrial ring electrode 17 and the pacemaker encapsulation 14.

FIG. 3 shows a further current path that is advantageous because it provides improved sensitivity to volume changes of the right atrium 3. The impedance measurement means 9 injects an impedance measurement current via an atrial lead formed by the atrial electrode 4, the atrial lead body 5, the atrial ring electrode 17 (as a first atrial ring electrode), and a second atrial ring electrode 18. The measurement current is injected to the atrium by the electrode 4 and the pacemaker encapsulation 14 is used as the return electrode. The voltage between the ring electrodes 17 and 18 is measured and this voltage represents a measure of the atrial impedance which reflects the atrial volume. A higher volume is indicated by a lowered impedance which in turn indicates increased atrial distension.

The atrial impedance can be monitored in many alternative ways. One possibility is to use the pacing pulses for impedance measurement in the atrium 3. This is particularly suitable when the patient suffers from atrial fibrillation since pacing pulses will not capture the atrium 3 under those circumstances.

The invention can also be used for monitoring the degree of atrial distension over an extended period of time to be able to follow the disease development and to enable the physician to adapt therapy accordingly. In that case the end diastolic atrial impedance would be measured several times per day. The result may be presented as average values of atrial impedance or atrial distension. The averaging period may range from 3 hours up to approximately 200 hours. This monitoring method can also be used when the heart is in atrial fibrillation in which case the average atrial impedance is monitored.

Although modifications and changes may be suggested by those skilled in the art, it is the invention of the inventor to embody within the patent warranted heron all changes and modifications as reasonably and properly come within the scope of his contribution to the art.

I claim as my invention:

1. An implantable pacemaker comprising:
    a pulse generator adapted to interact with at least one ventricle of a heart to deliver pacing pulses to that ventricle;
    a cardiac signal detector adapted to interact with the heart to detect cardiac signals originating from an atrium of the heart;
    an arrhythmia detector connected to the cardiac signal detector that analyzes said cardiac signals to detect an occurrence of atrial arrhythmia;
    an impedance measuring unit adapted to interact with said atrium to measure an atrial impedance therein; and
    a controller connected to said pulse generator, said arrhythmia detector and said impedance measuring unit, said controller being configured to control said pulse generator to cause said pulse generator to deliver said pacing pulses to the ventricle in a P-wave synchronous mode as long as no atrial arrhythmia is detected by said arrhythmia detector, and to switch control of said pulse generator to a non-P-wave synchronous mode if atrial arrhythmia is detected by said arrhythmia detector, and to determine an atrial distention of said atrium from the atrial impedance measured by said impedance measuring unit and, in said non-P-wave synchronous mode, to control said pulse generator to increase a delivery rate of said pacing pulses to an increased delivery rate that said controller, by continuing to evaluate said atrial impedance measured by said impedance measuring unit, is determined by said controller to decrease said atrial distention during said atrial arrhythmia.

2. An implantable pacemaker as claimed in claim 1, further comprising:
    a pacemaker housing containing said pulse generator, said cardiac signal detector, said impedance measurement unit, said arrhythmia detector and said controller, said pacemaker housing having an electrically conductive area exposed to tissue;
    a bipolar atrial lead connected to said pulse generator, said bipolar atrial lead comprising an atrial lead body carrying an atrial lead body carrying an atrial electrode and a ring electrode; and
    said impedance measuring unit injecting an impedance measurement current into the atrium through said atrial electrode and using said electrically conductive area of said housing as a return electrode, by measuring a voltage representing said atrial impedance between said atrial electrode and said housing.

3. An implantable pacemaker as claimed in claim 1, further comprising:
    a housing containing said pulse generator, said cardiac signal detector, said impedance measuring unit, said arrhythmia detector and said controller, said pacemaker housing having an electrically conductive area exposed to tissue;
    a tripolar atrial lead connected to said pulse generator, said tripolar atrial lead comprising an atrial lead body, adapted for implantation in the right atrium of the heart, carrying a first ring electrode and a second ring electrode; and said impedance measuring unit injecting an atrial impedance measurement current into the atrium through said atrial electrode and using said electrically conductive area of said housing as a return electrode, and measuring a voltage representing said atrial impedance between said first and second ring electrodes.

4. An implantable pacemaker as claimed in claim 1 wherein said controller is configured to control said pulse generator to deliver said pacing pulses to the ventricle at a delivery rate controlled in a closed loop by varying the delivery rate to maintain said atrial impedance substantially equal to a reference value, with said measured delivery rate that decreases said atrial distention during atrial arrhythmia occurring when said atrial impedance equals said reference value.

5. An implantable pacemaker as claimed in claim 1 wherein said controller is configured to repetitively store successively obtained values of said atrial distention and averages said values over a predetermined period of time.

* * * * *